United States Patent [19]
Beers et al.

[11] Patent Number: 6,040,320
[45] Date of Patent: Mar. 21, 2000

[54] 2-SUBSTITUTED IMIDAZOLES USEFUL IN THE TREATMENT OF INFLAMMATORY DISEASES

[75] Inventors: Scott A. Beers; Elizabeth A. Malloy, both of Flemington; Michael P. Wachter, Bloomsbury; Wei Wu, Somerville, all of N.J.

[73] Assignee: Ortho-McNeil Pharmaceutical, Inc., Raritan, N.J.

[21] Appl. No.: 09/106,698

[22] Filed: Jun. 29, 1998

Related U.S. Application Data

[60] Provisional application No. 60/051,301, Jun. 30, 1997.

[51] Int. Cl.⁷ .................. A61K 31/44; C07D 401/04
[52] U.S. Cl. ........................... 514/341; 546/274.1
[58] Field of Search ................ 546/274.1; 514/341

[56] References Cited

U.S. PATENT DOCUMENTS

| | | | |
|---|---|---|---|
| 3,772,441 | 11/1973 | Lombardino et al. | 514/341 |
| 3,929,807 | 12/1975 | Fitz | 514/341 |
| 3,940,486 | 2/1976 | Fitzi | 514/341 |
| 4,159,338 | 6/1979 | Cherkofsky et al. | 546/256 |
| 4,175,127 | 11/1979 | Bender et al. | 546/274.1 |
| 4,182,769 | 1/1980 | Cherkofsky et al. | 548/336 |
| 4,190,666 | 2/1980 | Cherkofsky et al. | 548/337 |
| 4,272,543 | 6/1981 | Niedballa et al. | 546/256 |
| 4,330,552 | 5/1982 | Cherkofsky | 548/337 |
| 4,348,404 | 9/1982 | Whitney | 548/342 |
| 4,372,964 | 2/1983 | Adams et al. | 546/256 |
| 4,440,776 | 4/1984 | Niedballa et al. | 548/337 |
| 4,503,065 | 3/1985 | Wilkerson | 514/396 |
| 4,528,298 | 7/1985 | Niedballa et al. | 514/398 |
| 4,608,382 | 8/1986 | Ferrini et al. | 514/341 |
| 4,780,470 | 11/1988 | Bender et al. | 514/341 |
| 5,593,991 | 1/1997 | Adams et al. | 514/235 |
| 5,593,992 | 1/1997 | Adams et al. | 514/235 |
| 5,633,377 | 5/1997 | Thurkauf et al. | 544/370 |
| 5,656,644 | 8/1997 | Adams et al. | 514/341 |
| 5,670,527 | 9/1997 | Adams et al. | 514/341 |
| 5,686,455 | 11/1997 | Adams et al. | 514/256 |

FOREIGN PATENT DOCUMENTS

| | | |
|---|---|---|
| 374198 | 4/1979 | Austria . |
| 0522887A1 | 7/1992 | European Pat. Off. . |
| 60232527 | 10/1985 | Japan . |
| 61155456 | 7/1986 | Japan . |
| 62032178 | 2/1987 | Japan . |
| 92/04330 | 3/1992 | WIPO . |
| 95/03297 | 2/1995 | WIPO . |
| 96/21452 | 7/1996 | WIPO . |

OTHER PUBLICATIONS

Charles, A. Dinarello, Inflammatory cytokines: interleukin–1 and tumor necrosis factor as Effector molecules in autoimmune diseases, Immunology 1991, 3:941–948.

Jeffrey C. Boehm et al., 1–Substituted 4–Aryl–5–pyridinylimidazoles: A New Class of Cytokine Suppressive Drugs with Low 5–Lipoxygenase and Cyclooxygenase Inhibitory Potency, J. Med Chem., 1996, 39, 3929–3937.

Alison M. Badger et al., Pharmacological Profile of SB 203580, a Selective Inhibitor of Cytokine Suppressive Binding Protein/p38 Kinase, in Animal Models of Arthritis, Bone Resorption, Endotoxin Shock and Immune Function, The Journal of Pharmacology and Experimental Therapeutics 279 1453–1461, 1996.

Michael J. Elliott et al., Treatment of Rheumatoid Arthritis with Chimeric Monoclonal Antibodies to Tumor Necrosis Factor, Arthritis & Rheumatism vol. 36 No.12, Dec. 1993, pp.1681–1690.

Don E. Griswold and Peter R. Young, Pharmacology of Cytokine Suppressive Anti–Inflammatory Drug Binding Protein (CSBP), a Novel Stress–Induced Kinase, Pharmacology Communications, 1996, vol. 7, pp. 323–329.

*Primary Examiner*—Jane Fan
*Attorney, Agent, or Firm*—John Harbour

[57] ABSTRACT

This invention relates to substituted imidazoles of Formula I

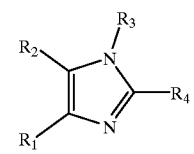

pharmaceutical compositions containing them, methods of using them and intermediates useful in their manufacture. The compounds of the invention modulate the production of a number of inflammatory cytokines, and are useful in the treatment of diseases associated with the production of inflammatory cytokines.

10 Claims, No Drawings

2-SUBSTITUTED IMIDAZOLES USEFUL IN THE TREATMENT OF INFLAMMATORY DISEASES

This application claims under 35 USC 119e 60/051,301 filed Jun. 30, 1997.

This invention relates to a series of substituted imidazoles, pharmaceutical compositions containing them and intermediates used in their manufacture. The compounds of the invention inhibit the production of a number of inflammatory cytokines, particularly, TNF-α, and IL-1β. Compounds of this invention are useful in the treatment of diseases associated with overproduction of inflammatory cytokines, such as rheumatoid arthritis, inflammatory bowel disease, septic shock, osteoporosis, and osteoarthritis.

BACKGROUND OF THE INVENTION

The inflammatory cytokines, IL-1β and TNF-α play an important role in a number of inflammatory diseases such as rheumatoid arthritis. C. Dinarello et al,. Inflammatory cytokines: Interleukin-1 and Tumor Necrosis Factor as Effector Molecules in Autoimmune Diseases *Curr. Opin. Immunol.* 1991, 3, 941–48. Arthritis is an inflammatory disease which affects millions of people and can strike at any joint of the human body. Its symptoms range from mild pain and inflammation in affected joints, to severe and debilitating pain and inflammation. Although the disease is associated mainly with aging adults, it is not restricted to adults. The most common arthritis therapy involves the use of nonsteroidal antiinflammatory drugs (NSAID) to alleviate the symptoms. However, despite their widespread use, many individuals cannot tolerate the doses necessary to treat the disease over a prolonged period of time. In addition, NSAIDs merely treat the symptoms of disease without affecting the underlying cause. Other drugs, such as methotrexate, gold salts, D-pencillamine, and prednisone are often used when patients fail to respond to NSAIDS. These drugs also have significant toxicities and their mechanism of action remain unknown.

Receptor antagonists to IL-1β and monoclonal antibodies to TNF-α have been shown to reduce symptoms of rheumatoid arthritis in small-scale human clinical trials. In addition to protein based therapies, there are small molecule agents which inhibit the production of these cytokines and have demonstrated activity in animal arthritis models. J. C. Boehm et al., 1-Substituted 4-Aryl-5-pyridinylimidazoles: A New Class of Cytokine Suppressive Drugs With Low 5-Lipoxygenase and Cyclooxygenase Inhibitory Potency, *J. Med. Chem.*, 1996, 39, 3929–37. Of these small molecule agents, SB 203580 has proved effective in reducing the production of TNF-α and IL-1 in LPS stimulated human monocyte cell lines with $IC_{50}$ values of 50 to 100 nM. J. Adams et al., Imidazole Derivatives And Their Use as Cytokine Inhibitor, International Patent application WO 93114081, Jul. 23, 1993. In addition to this in vitro test, SB 203580 inhibits the production of the inflammatory cytokines in rats and mice at $IC_{50}$ values of 15 to 25 mg/kg. A. M. Badger, et al, Pharmacological Profile of SB 203580, A Selective Inhibitor of Cytokine Suppressive Binding Protein/p38 Kinase, in Animal Models of Arthritis, Bone Resorption, Endotoxin Shock and Immune Function, *The Journal of Pharmacology and Experimental Therapeutics*, 1996, 279, 1453–61. Although human data is currently unavailable for SB 203580, monoclonal antibodies to TNF-α have proved efficacious in the treatment of rheumatoid arthritis. M. J. Elliot et al., Treatment of Rheumatoid Arthritis with Chimeric Monoclonal Antibodies to Tumor Necrosis Factor α, *Arthritis Rheum.* 1993 36, 1681–90. Due to SB 203580's oral activity and potency in animal models, researchers have suggested that a compound with this profile has potential as a viable treatment for rheumatoid arthritis. A. M. Badger, et al. Pharmacological Profile of SB 203580, A Selective Inhibitor of Cytokine Suppressive Binding Protein/p38 Kinase, in Animal Models of Arthritis, Bone Resorption, Endotoxin Shock and Immune Function, *The Journal of Pharmacology and Experimental Therapeutics*, 1996, 279,1453–61.

SB 203580 and other small molecule agents reduce the production of inflammatory cytokines by inhibiting the activity of a serine/threonin kinase p38 (note other researchers refer to this enzyme as CSBP), at an $IC_{50}$ of 200 nM. D. Griswold et al., Pharmacology of Cytokine Suppressive Anti-inflammatory Drug Binding Protein (CSPB), A Novel Stress-induced Kinase, *Pharmacology Communications*, 1996, 7, 323–29. Although the precise mechanism of this kinase is unknown, it has been implicated in both the production of TNF-α and the signaling responses associated with the TNF-α receptor.

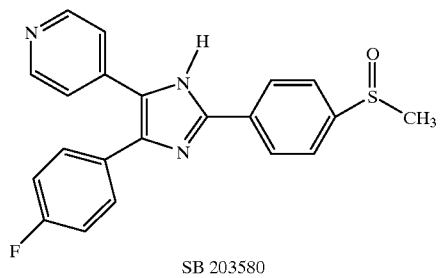

SB 203580

SUMMARY OF THE INVENTION

The invention relates to compounds of the Formula I

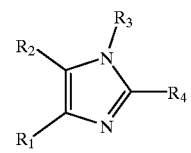

I wherein:

R₁ is phenyl, heteroaryl wherein the heteroaryl contains 5 to 6 ring atoms, or
   substituted phenyl
      wherein the substituents are independently selected from one or members of the group consisting of $C_{1-5}$alkyl, halogen, nitro, trifluoromethyl and nitrile;

R₂ is phenyl, heteroaryl wherein the heteroaryl contains 5 to 6 ring atoms,
   substituted heteroaryl
      wherein the substituents are independently selected from one or more members of the group consisting of $C_{1-5}$alkyl and halogen, or
   substituted phenyl
      wherein the substituents are independently selected from one or members of the group consisting of $C_{1-5}$alkyl, halogen, nitro, trifluoromethyl and nitrile;

R₃ is hydrogen, SEM, $C_{1-5}$alkoxycarbonyl, aryloxycarbonyl, aryl$C_{1-5}$alkyloxycarbonyl, aryl$C_{1-}$ $_5$alkyl, phthalimidoC$_{1-5}$alkyl, aminoC$_{1-5}$alkyl, diaminoC$_{1-5}$alkyl, succinimidoC$_{1-5}$alkyl, C$_{1-5}$alkylcarbonyl, arylcarbonyl, C$_{1-5}$alkylcarbonylC$_{1-5}$alkyl, aryloxycarbonylC$_{1-5}$alkyl, heteroarylC$_{1-5}$alkyl where the heteroaryl contains 5 to 6 ring atoms, or substituted arylC$_{1-5}$alkyl
  wherein the aryl substituents are independently selected from one or more members of the group consisting of C$_{1-5}$alkyl, C$_{1-5}$alkoxy, halogen, amino, C$_{1-5}$alkylamino, and diC$_{1-5}$alkylamino;

R$_4$ is (A)$_n$-(CH$_2$)$_q$-X wherein:
A is sulfur or carbonyl;
n is 0 or 1;
q is 0–9;
X is selected from the group consisting of hydrogen, hydroxy, halogen, vinyl, ethynyl, C$_{1-5}$alkyl, C$_{3-7}$cycloalkyl, C$_{1-5}$alkoxy, phenoxy, phenyl, arylC$_{1-5}$alkyl, amino, C$_{1-5}$alkylamino, nitrile, phthalimido, amido, phenylcarbonyl, C$_{1-5}$alkylaminocarbonyl, phenylaminocarbonyl, arylC$_{1-5}$alkylaminocarbonyl, C$_{1-5}$alkylthio, C$_{1-5}$alkylsulfonyl, phenylsulfonyl, substituted sulfonamido
  wherein the sulfonyl, substituent is selected from the group consisting of C$_{1-5}$alkyl, phenyl, araC$_{1-5}$alkyl, thienyl, furanyl, and naphthyl;
substituted vinyl
  wherein the substituents are independently selected from one or members of the group consisting of fluorine, bromine, chlorine and iodine,
substituted ethynyl
  wherein the substituents are independently selected from one or more members of the group consisting of fluorine, bromine chlorine and iodine,
substituted C$_{1-5}$alkyl
  wherein the substituents are selected from the group consisting of one or more C$_{1-5}$alkoxy, trihaloalkyl, phthalimido and amino,
substituted phenyl
  wherein the phenyl substituents are independently selected from one or more members of the group consisting of C$_{1-5}$alkyl, halogen and C$_{1-5}$alkoxy,
substituted phenoxy
  wherein the phenyl substituents are independently selected from one or more members of the group consisting of C$_{1-5}$alkyl, halogen and C$_{1-5}$alkoxy,
substituted C$_{1-5}$alkoxy
  wherein the alkyl substituent is selected from the group consisting of phthalimido and amino,
substituted arylC$_{1-5}$alkyl
  wherein the alkyl substituent is hydroxyl,
substituted arylC$_{1-5}$alkyl
  wherein the phenyl substituents are independently selected from one or more members of the group consisting of C$_{1-5}$alkyl, halogen and C$_{1-5}$alkoxy,
substituted amido
  wherein the carbonyl substituent is selected from the group consisting of C$_{1-5}$alkyl, phenyl, arylC$_{1-5}$alkyl, thienyl, furanyl, and naphthyl;
substituted phenylcarbonyl
  wherein the phenyl substituents are independently selected from one or members of the group consisting of C$_{1-5}$alkyl, halogen and C$_{1-5}$alkoxy,
substituted C$_{1-5}$alkylthio
  wherein the alkyl substituent is selected from the group consisting of hydroxy and phthalimido,
substituted C$_{1-5}$alkylsulfonyl
  wherein the alkyl substituent is selected from the group consisting of hydroxy and phthalimido,
substituted phenylsulfonyl
  wherein the phenyl substituents are independently selected from one or members of the group consisting of bromine, fluorine, chlorine, C$_{1-5}$alkoxy and trifluoromethyl,
with the proviso:
  if A is sulfur and X is other than hydrogen, C$_{1-5}$alkylaminocarbonyl, phenylaminocarbonyl, arylC$_{1-5}$alkylaminocarbonyl, C$_{1-5}$alkylsulfonyl or phenylsulfonyl, then q must be equal to or greater than 1;
  if A is sulfur and q is 1, then X cannot be C$_{1-2}$alkyl;
  if A is carbonyl and q is 0, then X cannot be vinyl, ethynyl, C$_{1-5}$alkylaminocarbonyl, phenylaminocarbonyl, arylC$_{1-5}$alkylaminocarbonyl,C$_{1-5}$alkylsulfonyl or phenylsulfonyl;
  if A is carbonyl, q is 0 and X is H, then R$_3$ is not SEM;
  if n is 0 and q is 0, then X cannot be hydrogen;
and pharmaceutically acceptable salts thereof.

In addition this invention contemplates pharmaceutical compositions containing compounds of Formula I, and methods of treating cytokine mediated disorders with compounds of Formula I.

The novel compounds of this invention inhibit the in vitro activity of p-38 in the nanomolar range. In addition, the compounds inhibit the in vitro secretion of TNF-α and IL-1β in the nanomolar range. Animal models demonstrate the inhibition of LPS induced TNF-α, as well as the inhibition of rheumatoid arthritis. With this range of activity the compounds of the invention are useful in the treatment of a variety of cytokine related disorders including: rheumatoid arthritis, inflammatory bowel disease, septic shock osteoporosis, osteoarthritis, neuropathic pain, HIV replication, HIV dementia, viral myocarditis, insulin-dependent diabetes, non-insulin dependent diabetes, periodontal disease, restenosis, alopecia areta, T-cell depletion in HIV infection or AIDS, psoriasis, acute pancreatitis, allograft rejection, allergic inflammation in the lung, atherosclerosis, mutiple sclerosis, cachexia, alzheimer's disease, stroke, Crohn's disease, inflammatory bowel disease, ischemia, congestive heart failure, pulmonary fibrosis, hepatitis, glioblastoma, Guillain-Barre Syndrome, and systemic lupus erythematosus.

DETAILED DESCRIPTION OF THE INVENTION

The terms used in describing the invention are commonly used and known to those skilled in the art. However, the terms that could have other meanings are defined. The term "FCS" represents fetal calf serum, "TCA" represents trichloroacetic acid and the "RPMI" represents the medium from the Roswell Park Memoria Inst. (Sigma cat # R0833). "Independently" means that when there are more than one substituent, the substitutents may be different. The term "alkyl" refers to straight, cyclic and branched-chain alkyl groups and "alkoxy" refers O-alkyl where alkyl is as defined supra. The term heteroaryl refers to an aromatic ring of five or six members where at least one member is a heteroatom. Suitable heteroatoms include, nitrogen, oxygen and sulfur. In the case of five-membered rings the heteroaryl will contain one sulfur, oxygen, or nitrogen atom and, in addition, may contain up to three additional nitrogens. With six-membered rings the heteroaryl may contain up to three nitrogens. Examples of such heteroaryls include, pyridin-2-yl, pyridin-3-yl, pyridin4-yl, pyrimidin-3-yl, furan-2-yl, furan-3-yl, thiophen-2-yl, thiophen-3-yl, pyridazine, triazine, thiazole, oxazole, pyrazole and the like. "SEM" refers to 2-(trimethylsilyl)ethoxymethyl) and "LDA" refers to lithium diisopropylamide. The symbol "Ph" refers to phenyl, "PHT" refers to phthalimido and the "aryl" includes mono and fused aromatic rings such as phenyl and naphthyl.

As used in this invention the term "cytokine" refers to the proteins TNF-α and IL-1β. Cytokine related disorders are diseases of humans and other mammals where the overproduction of cytokines causes the symptoms of the disease. The overproduction of the cytokines, TNF-α and IL-1β has been linked to a number of diseases. These cytokine related disorders include but are not limited to rheumatoid arthritis, inflammatory bowel disease, septic shock osteoporosis, osteoarthritis, neuropathic pain, HIV replication, HIV dementia, viral myocarditis, insulin-dependent diabetes, non-insulin dependent diabetes, periodontal disease, restenosis, alopecia areta, T-cell depletion in HIV infection or AIDS, psoriasis, actue pancreatitis, allograft rejection, allergic inflammation in the lung, atherosclerosis, mutiple sclerosis, cachexia, alzheimer's disease, stroke, Crohn's disease, inflammatory bowel disease, ischemia, congestive heart failure, pulmonary fibrosis, hepatitis, glioblastoma, Guillain-Barre Syndrome, and systemic lupus erythematosus. The term "effective dose" refers to an amount of a compound of Formula I which reduces the amount of TNFα and/or IL-1β which may be detected in a mammal suffering from a cytokine mediated disorder. In addition, the term "effective dose" refers to an amount of a compound of Formula I which reduces the symptoms of a cytokine related disorder.

The compounds of the invention may be prepared by the following schemes, where some schemes produce more than one embodiment of the invention. In those cases, the choice scheme is a matter of discretion that is well within the capabilities of those skilled in the art.

Scheme I may be used to produce the compounds of the invention where A is sulfur. The starting material for this scheme is a mercapto imidazole as exemplified by intermediate 1a. This intermediate may be prepared following known imidazole preparations. Lantos, I. et al. *J. Org. Chem*, 1988, 53, 4223–27; Markova, Y. et al. *Zh. Org. Zhim.* 1965, 1, 1475. Intermediate 1a is treated with a base such as NaH, or n-BuLi in an inert solvent such as DMF or THF at room temperature over 30 minutes to several hours. This reaction mixture is treated with an alkylating agent such as 1-bromopentane to give the desired compound 1b. This reaction sequence may be used to produce the compounds of the invention where A is sulfur, n is 1, q is 0–9 and X is hydrogen, vinyl, ethynyl, substituted ethynyl, $C_{1-5}$alkyl, $C_{3-7}$cycloalkyl, substituted $C_{1-5}$alkyl, $C_{1-5}$alkoxy, aryl$C_{1-5}$alkyl, substituted aryl$C_{1-5}$alkyl, nitrile or $C_{15}$alkylamino, by modifying the alkylating agent with known compounds. For example to produce a compound of the invention where A is sulfur, n is 1 q is 0 and X is aryl$C_{1-5}$alkyl, one may treat intermediate 1a with benzyl chloride.

To produce the compounds of the invention where A is sulfur, n is 1, q is 0 and X is phenylaminocarbonyl, intermediate 1a is treated with a base such as NaH, or n-BuLi in an inert solvent such as DMF or THF at room temperature over 30 minutes to several hours. This reaction mixture is treated with an isocyanate, such as phenylisocyanate at room temperature over 1 to 24 hours. This reaction sequence may be used to produce the compounds 1 c of the invention where A is sulfur, n is 1, q is 0 and X is $C_{1-5}$alkylaminocarbonyl by using known isocyanates. In addition, this sequence may be used to produce compounds where X is phenylcarbonyl, substituted phenylcarbonyl and $C_{1-5}$alkylcarbonyl. Replacement of the isocyanate with a known substituted acyl halide derivative, such as 2-bromoacetophenone, gives the compound of the invention where X is phenylcarbonyl.

The compounds of the invention where A is sulfur, n is 1, q is 1 and X is nitrile may be produced as illustrated in Scheme I. Intermediate 1a is treated with a base such as NaH, or n-BuLi in an inert solvent such as DMF or THF at room temperature over 30 minutes to several hours. This reaction mixture is treated with an acetonitrile derivative such as iodoacetonitrile over several hours at room temperature to give compounds of the type 1d. In addition to compounds of the type 1d, one may use this sequence to produce compounds where A is sulfur, n is 1, q is 1 or greater and X is vinyl or ethynyl. These compounds may be prepared by replacing iodoacetonitrile with allyl halides or propargyl halides respectively.

Scheme I may be used to produce compounds of the invention where A is sulfur, n is 1, q is greater than 1 and X is phthalimido. Intermediate I a is treated with a bases such as NaH, or n-BuLi in an inert solvent such as DMF or THF at room temperature over 30 minutes to several hours. This reaction mixture is treated with an haloalkylphthalimido derivative for 1 to several hours to give compounds of type 1e. To produce compounds where X is amino, compounds of type 1e are treated with hydrazine to give compounds of type 1f.

SCHEME 1

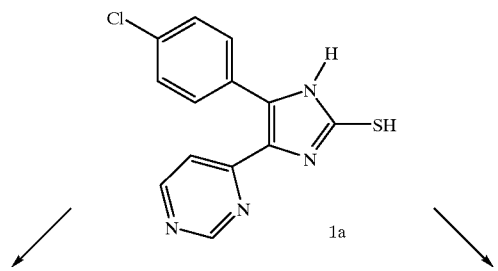

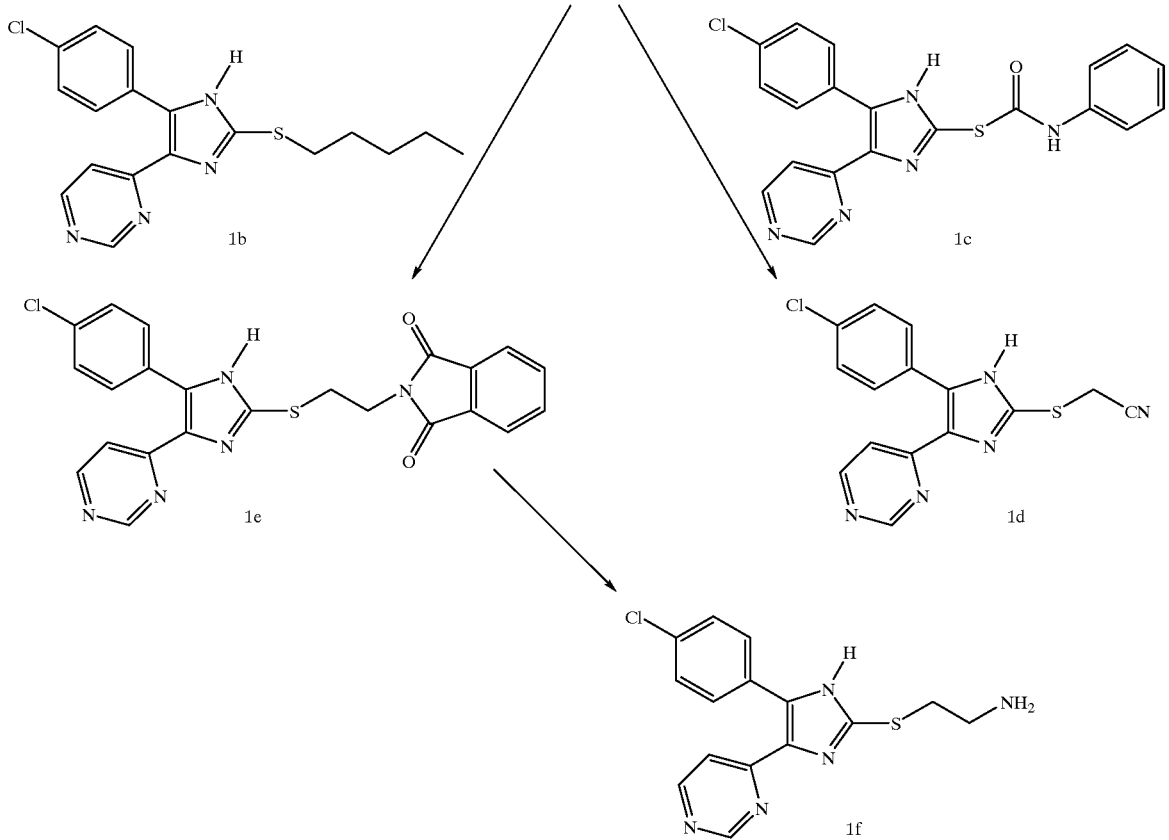

Other compounds of the invention may be produced via Scheme 2 using compounds of type If as starting materials. Compound If and furoyl chloride are treated with a mild base such as sodium bicarbonate and an inert solvent, such as DMF, at room temperature for 1 to several hours to give compounds of type 2a.

The compounds of the invention where X is carbonyl substituted amido, may be prepared via this method. For example, to prepare a compound where where A is sulfur, n is 1, q is 2 and X is naphth-2-ylamido, 2-naphthoyl chloride may be used in place of furoyl chloride to give the desired compound. In addition, this scheme may be used to prepare compounds where X is substituted sulfonamido of the type 2b. Replacement of furoyl chloride by propanesulfonyl chloride gives compounds of type 2b.

SCHEME 2

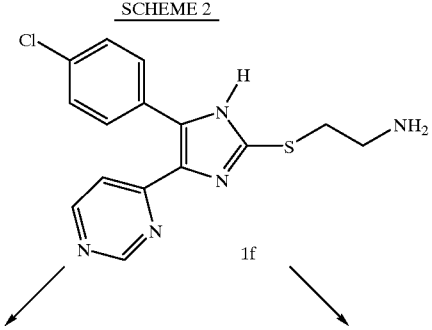

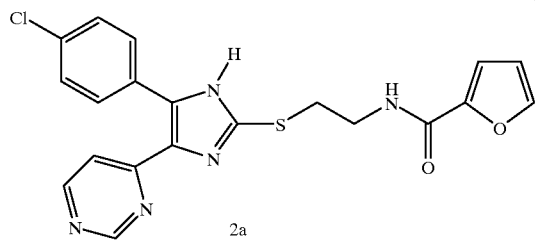

2a

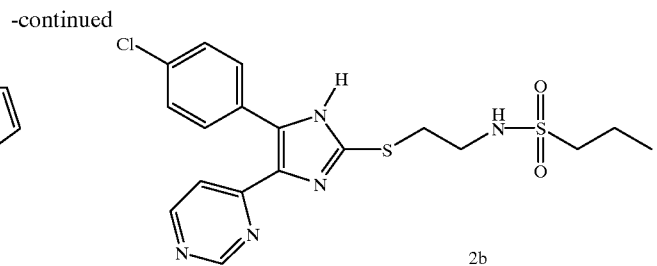

2b

To produce the compounds of the invention where A is carbonyl, n is 1, q is 0 and X is hydrogen, Scheme 3 may be used. The starting imidazole, 3a, may be prepared following literature preparations (See eg., Klaus Hofmann, Imidazole and Its Derivatives Part I (1953)). This material is treated with bases such as NaH, or n-BuLi in an inert solvent such as DMF or THF at room temperature over 15 minutes to several hours. This reaction mixture is treated with a nitrogen protecting group which is stable to basic conditions, such as 2,2-(trimethylsilyl)ethoxymethyl chloride at room temperature over 1 to 24 hours to give the 1-substituted imidazoles 3b$_1$ and 3b$_2$ The isomers 3b$_1$ and 3b$_2$ may be independently treated with a base, such as n-BuLi, and an inert solvent, such at THF, at about −78 ° C. under an inert atmosphere for about 15–30 min. This mixture is treated with a formylating agent, such as DMF, at room temperature for about 1 h to give compounds of type 3c. Treatment of intermediate 3c with an aqueous acid such as 1 N HCl at room temperature for about 30 min to several hours gives 3d. This reaction sequence may be used to produce the compounds of the invention where A is carbonyl, q is 0–9, and X is C$_{1-5}$alkyl, phenyl and arylC$_{1-5}$alkyl by replacing the formylating agent with an acylating agent. For example to prepare a compound where A is carbonyl, q is 1, and X is phenyl, replace the formylating agent with benzoyl chloride. In addition compounds where A is carbonyl, q is 0–9 and X is hydroxy can be prepared by replacing the alkylating agent with cyclic lactones. For example, to prepare a compound where A is carbonyl, q is 3 and X is hydroxy, intermediate 3a is treated with butyrolactone.

SCHEME 3

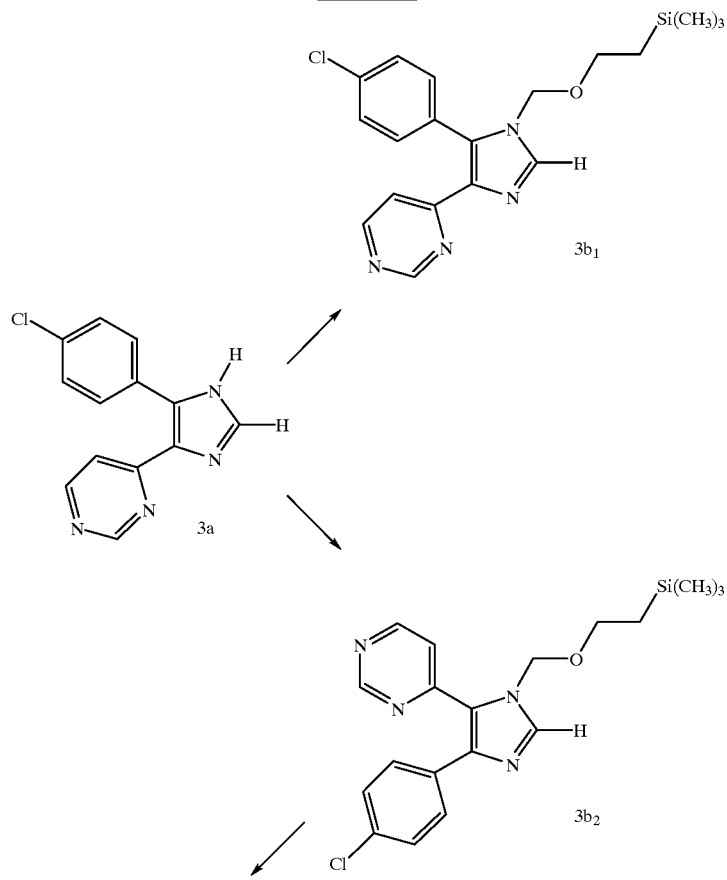

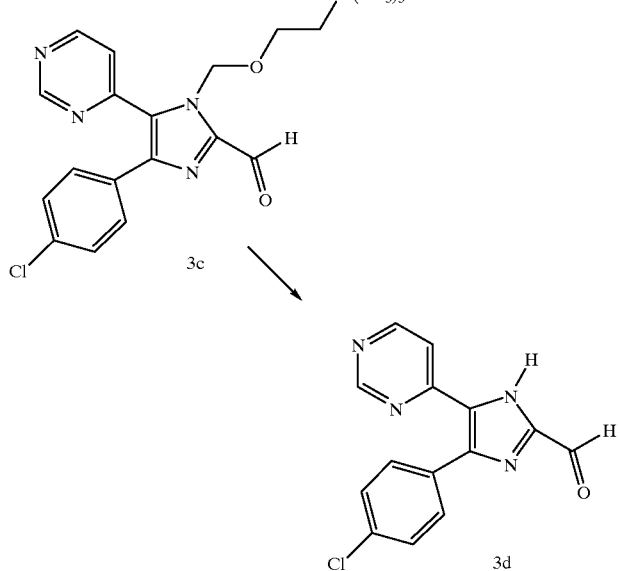

To prepare compounds of the invention where n is 0, intermediates from Scheme 3, may be used in Scheme 4. Intermediate 3c may be treated with $H_2$ and a hydrogenation catalyst such as Pd/C, at room temperature over 1 to several hours to give the alcohol 4a. This alcohol may be activated with triphenylphosphine or carbon tetrachloride and displaced with a nucleophilic agent such as 2-propanethiol at room temperature for 15 to 48 hours to give compounds of formula 4b. Treatment of 4b with aqueous acids such as 1 N HCI at room temperature over several hours gives compounds of type 4c. This scheme may be used to produce compounds where X is substituted amino by modifying the nucleophilic agent. For example if one replaces 2-propanethiol with propylamine, a compond where n is 0, q is 1 and X is propylamino may be prepared.

Aside from nucleophilic displacement, alcohol 4a may be may be treated with aqueous acids such as 1N HCI at room temperature over several hours to give the unprotected alcohol 4d. This unprotected alcohol may be used to prepare other compounds of the invention. For example, to prepare a compound where n is 0, q is 1 and X is $C_{1-5}$alkoxy, compound 4d is treated with a base such as NaH and an alkylating agent such as propyl bromide at room temperature.

SCHEME 4

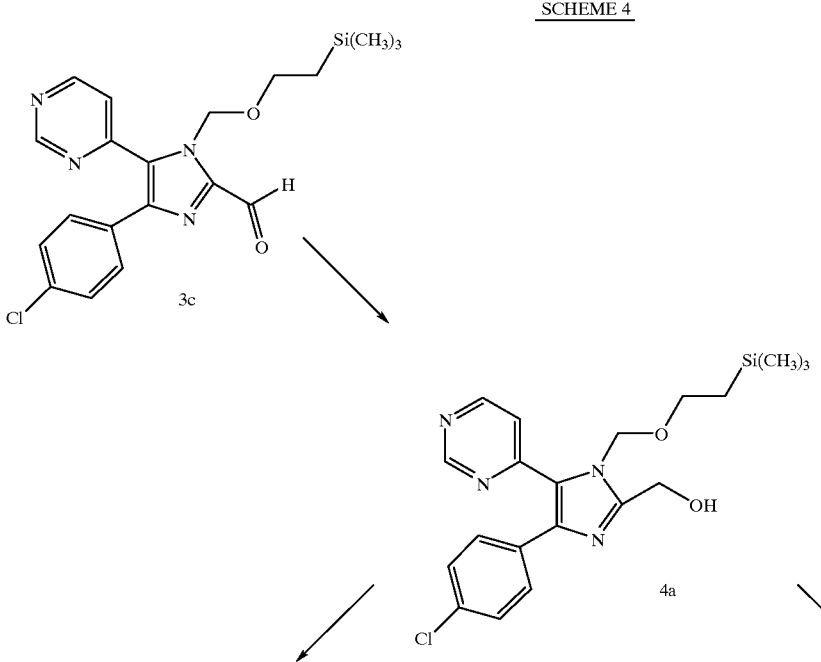

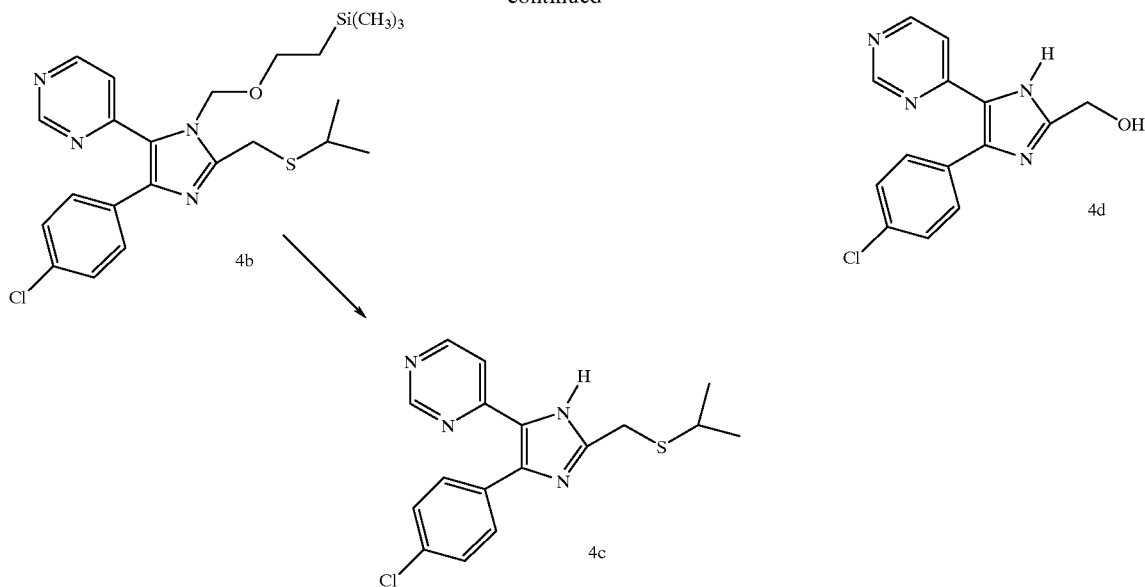

To prepare compounds where n is 0 and X is $C_{1-5}$alkylsulfonyl or alkyl substituted $C_{1-5}$alkylsulfonyl, Scheme 5 may be used. Intermediate 4a is treated with a hydroxyl activating group, such as triphenylphosphine and carbon tetrachloride in an inert solvent, such as acetonitrile. The activated intermediate is treated with a alkylating group such as 2-mercaptopropanol and an organic or inorganic base such as NaOH at about room temperature to reflux for several hours to give intermediates of the type 5a. As discussed previously, intermediate 5a may be treated with acidic solutions to give imidazol-2-yl substituted compounds of type 5b. Alternatively, intermediate 5a may be treated with oxidizing agents such as oxone in an inert solvent such as MeOH at ambient temperature over about 4–14 hours to give sulfones of type 5c. Finally intermediates such as 5c may be treated with aqueous acid solutions to give imidazol-2-yl substituted compounds of type 5d.

SCHEME 5

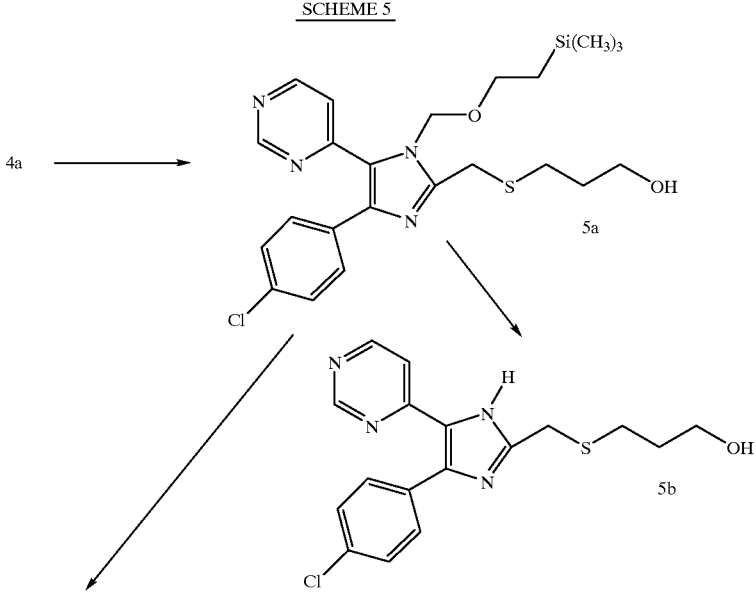

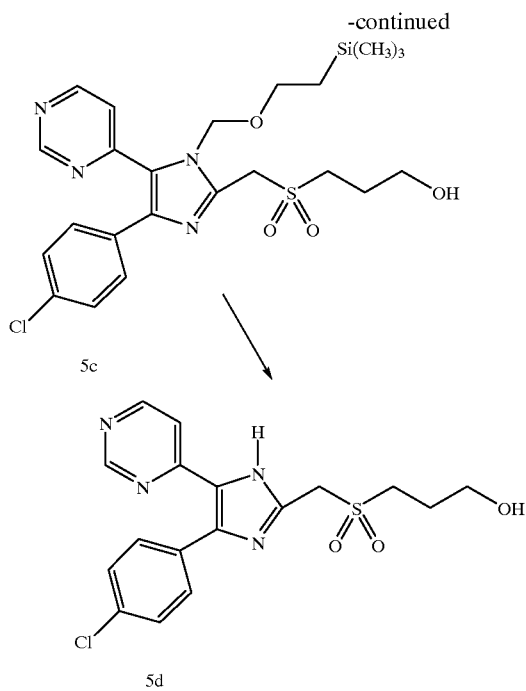

5c

5d

Although the preceding schemes start with an unsubstituted imidazole ring, many of the compounds of the invention may be prepared by forming the imidazole with the desired 2-substitution as illustrated by Scheme 6. In this scheme, a dione of type 6a, such as 1-(4-chlorophenyl)-2-(4-pyrimidinyl)-2-ethandione is treated with an aldehyde such as ethoxypropionaldehyde, ammonium acetate and acetic acid at about 70° C. to reflux for several hours. The desired compound is isolated from this mixture to give a compound of the type 6b. This scheme may be used to produce compounds of the invention where n is 0, q is 1–9 and X is H, phthalimido and $C_{1-5}$alkoxy.

SCHEME 6

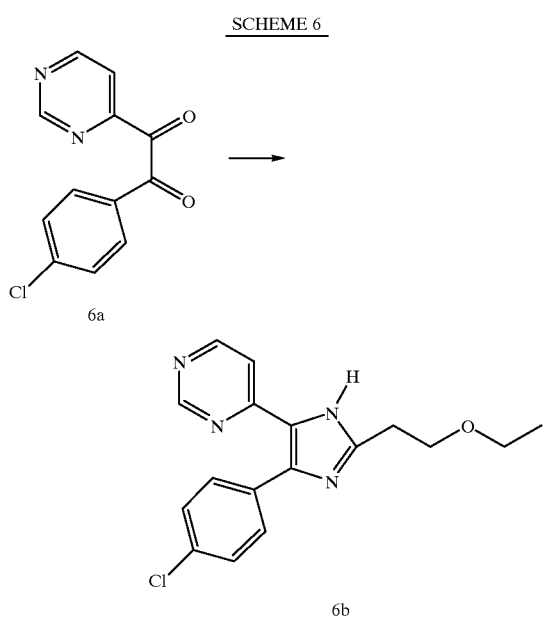

6a

6b

In order to produce compounds of the invention where $R_3$ is other than hydrogen or SEM, the final products of Schemes 1–6 may be treated with a base such as NaH, n-BuLi or $K_2CO_3$ in an inert solvent such as DMF or THF at room temperature over 15 minutes to several hours. The resulting anion may be treated with an appropriate alkylating or acylating agent. For example, to produce compounds of the invention where $R_3$ is arylcarbonyl, A is sulfur and X is pentyl, compounds of the type 1b may be treated with NaH, followed by benzoyl chloride.

In order to produce the compounds of the invention where n is 0, q is 0 and X is halogen, Scheme 7 may be used. The starting material for the scheme is a 4,5-disubstituted imidazole of the type 7a. Substituted imidazoles may be prepared following know procedures and the substituents $R_1$ and $R_2$ of the compounds of the invention are determined by the substituents of intermediate 7a. Intermediate 7a is treated with a base, such as NaH and an inert solvent such as DMF at room temperature for about 30 min to 1 h. Once anion formation is complete, an alkylating agent is added such as phenethyl chloride and the reaction mixture is stirred at about 60–100° C. for about 2–4 h to give intermediates $7b_1$ and $7b_2$. These intermediates are separated at this stage to allow for the formation of final products with one predominate isomer. Although the final products may be separated, the separation of $7b_1$ and $7b_2$ leads to higher yields of products.

Intermediate $7b_2$ is treated with a strong base such as LDA in an inert solvent such as THF at −78° C. for about 30 min. A source of halogen atoms such as iodine or bromine is added to the formed anion and this mixture is allowed to warm to ambient temperature over 30 min to 1 h to give intermediate 7c where X is iodine.

SCHEME 7
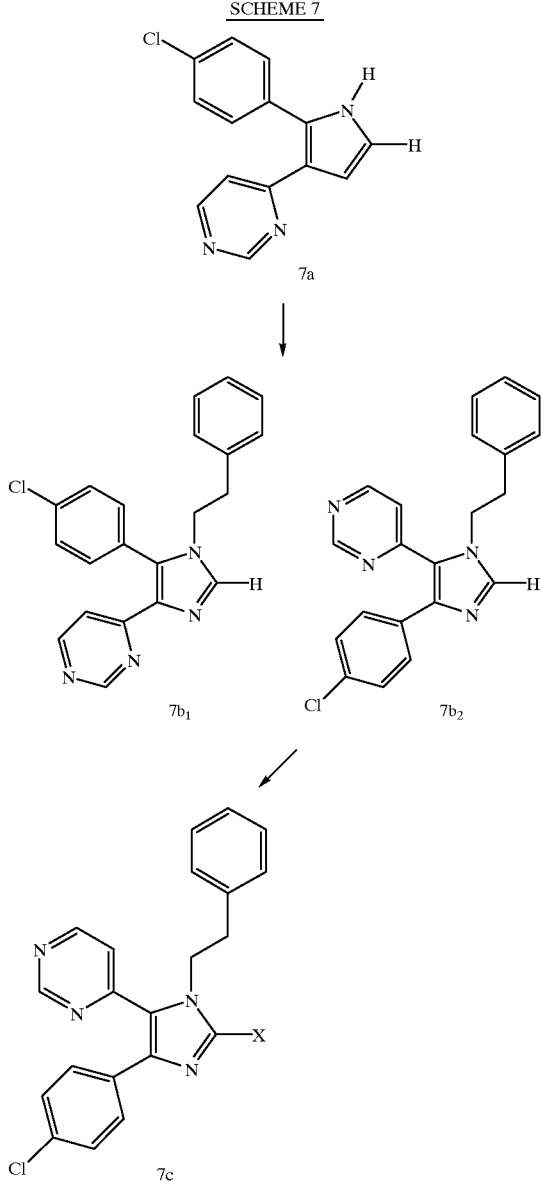
Although the claimed compounds are useful as inhibitors of TNF-α and IL-1, some compounds are more active that others and are either preferred or particularly preferred.
The preferred compound of Formula I include:
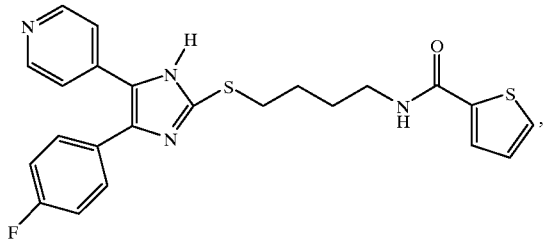
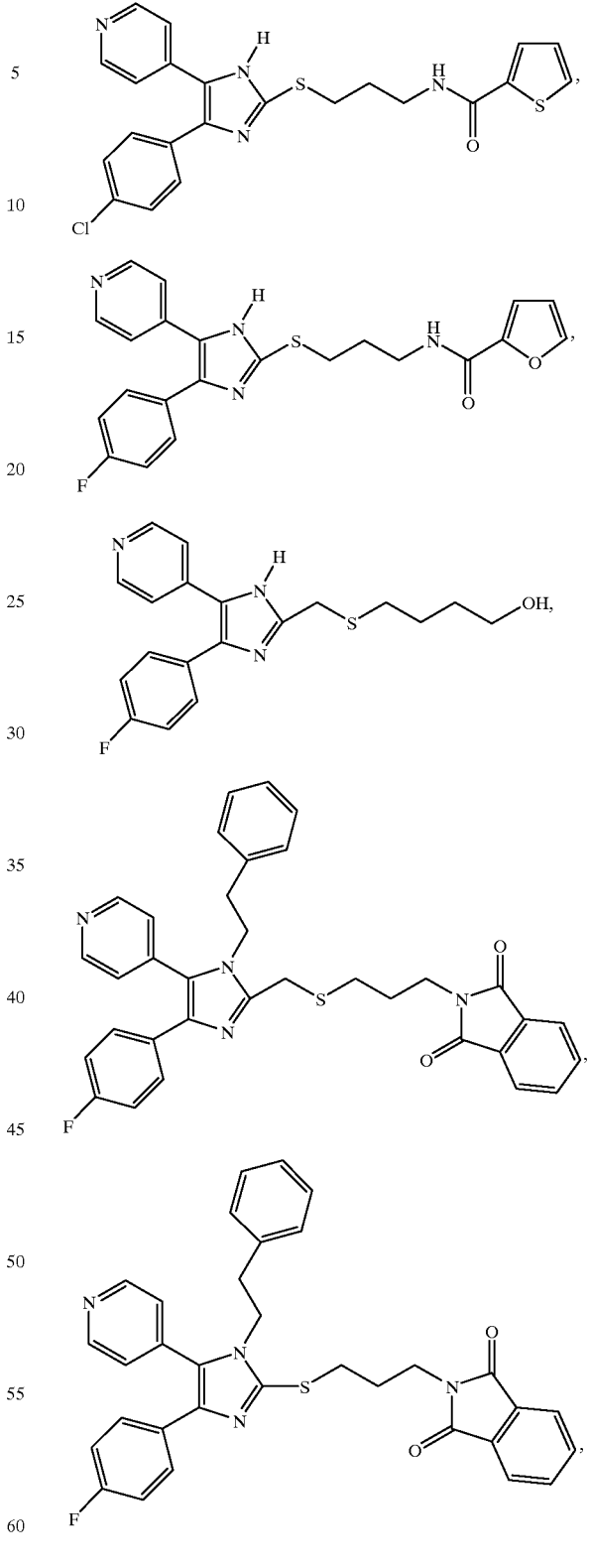

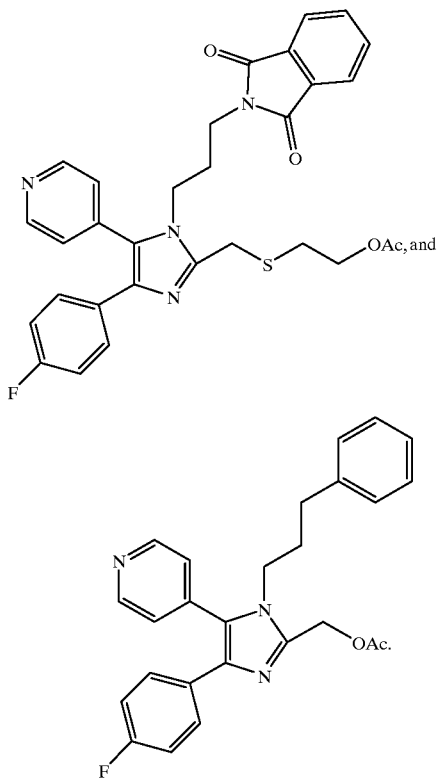

The particularly preferred "R$_1$"s are phenyl or substituted phenyl where the phenyl substituents are halogen and nitrile.

The particularly preferred "R$_2$"s are pyrid4-yl, pyrimidin4-yl and 2-butyl-pyrid4-yl.

The particularly preferred "R$_3$"s are hydrogen, SEM, C$_{1-5}$alkyl phenylC$_{1-5}$alkyl, and substituted phenylC$_{1-5}$alkyl.

The particularly preferred "q"s are 0–6.

The particularly preferred "X"s are hydrogen, hydroxy, nitrile, C$_{1-5}$alkyl, phthalimido, amido, substituted amido, C$_{1-5}$alkylsulfonyl, hydroxyC$_{1-5}$alkylsulfonyl, phenylsulfonyl, substituted phenylsulfonyl, substituted amido, substituted sulfonamido, C$_{1-5}$alkoxycarbonyloxy, and C$_{1-5}$alkyl.

Compounds of Formula I may be used in pharmaceutical compositions to treat patients (humans and other primates) with disorders related to the overproduction of inflammatory cytokines, particularly TNF-α. The preferred route is oral administration, however compounds may be administered by intravenous infusion or topical administration. Oral doses range from about 0.05 to 100 mg/kg, daily. Some compounds of the invention may be orally dosed in the range of about 0.05 to about 50 mg/kg daily, while others may be dosed at 0.05 to about 20 mg/kg daily. Infusion doses can range from about 1.0 to 1.0×10$^4$ µg/kg/min of inhibitor, admixed with a pharmaceutical carrier over a period ranging from several minutes to several days. For topical administration compounds of Formula I may be mixed with a pharmaceutical carrier at a concentration of about 0.1 to about 10% of drug to vehicle.

The pharmaceutical compositions can be prepared using conventional pharmaceutical excipients and compounding techniques. Oral dosage forms may be elixirs, syrups, capsules tablets and the like. Where the typical solid carrier is an inert substance such as lactose, starch, glucose, methyl cellulose, magnesium sterate, dicalcium phosphate, manni- tol and the like; and typical liquid oral excipients include ethanol, glycerol, water and the like. All excipients may be mixed as needed with disintegrants, diluents, granulating agents, lubricants, binders and the like using conventional techniques known to those skilled in the art of preparing dosage forms. Parenteral dosage forms may be prepared using water or another sterile carrier.

Typically the compounds of Formula I are isolated and used as free bases, however the compounds may be isolated and used as their pharmaceutically acceptable salts. Examples of such salts include hydrobromic, hydroiodic, hydrochloric, perchloric, sulfuric, maleic, fumaric, malic, tartatic, citric, benzoic, mandelic, methanesulfonic, hydroethanesulfonic, benzenesulfonic, oxalic, pamoic, 2-naphthalenesulfonic, p-toluenesulfonic, cyclohexane-sulfamic and saccharic.

In order to illustrate the invention the following examples are included. These examples do not limit the invention. They are only meant to suggest a method of practicing the invention. Those skilled in the art may find other methods of practicing the invention, which are readily apparent to them. However those methods are deemed to be within the scope of this invention.

SYNTHETIC EXAMPLES

Example 1

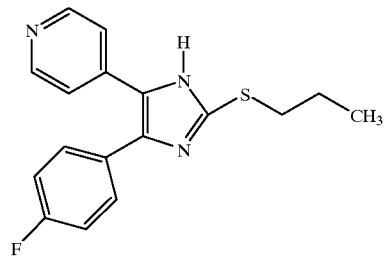

5(4)-(4-Fluorophenyl)2-(1-propyl)thio-4(5)-(4-pyridyl)-5(4)-imidazole

Cpd. 1

A slurry of 4-(4-fluorophenyl)-2-mercapto-5-(4-pyridyl) imidazole (0.52 g, 1.92 mmol: Lantos et al *Journal of Organic Chemistry,* 1988, 53, 4223–27), 95%NaH (48 mg, 1.92 mmol) and DMF (20 mL) was stirred under N$_2$ for 30 min at room temperature. 1-Iodopropane (0.19 mL,1.92 mmol) was added and the resulting solution was stirred at room temperature for 20h. The reaction mixture was poured into ice/H$_2$O (100 mL) and the resulting yellow solid was filtered and washed with H$_2$O. This solid was recrystallized form MeOH/H$_2$O (20:5) to give compound 1 as a yellow solid: mp 222–27° C.; MS (Cl$^+$) 314(M$^+$).

Example 2

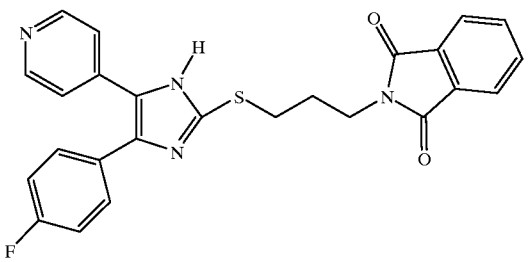

5(4)-(4-Fluorophenyl)-2-(3-phthalimidoprop-1-yl)thio-4(5)-(4-pyridyl)-imidazole

Cpd. 2

N-(3-bromopropyl)phthalimide (1.02 g, 3.8 mmol) and 60% NaH (0.152 g) were added to a solution of 4-(4-fluorophenyl)-2-mercapto-5-(4-pyridyl)-imidazolethione (1.03 g, 3.80 mmol) and the resulting mixture was stirred at room temperature for 1 h. The mixture was poured into ice/$H_2O$ and the resulting solid was washed with water and dried to give compound 2 as a solid: mp 241–43° C.; MS 459 ($MH^+$).

Example 3

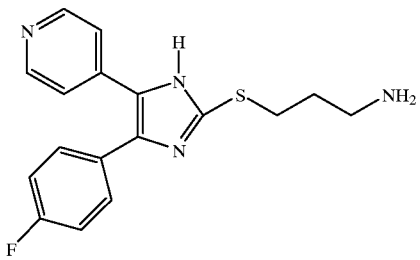

2-(3-Aminoprop-1-yl)thio-5(4)-(4-fluorophenyl)4(5)-(4-pyridyl)-imidazole

Cpd. 3

55% Hydrazine (1.1 mL) was added to a solution of compound 2 (4.40 g, 9.60 mmol) in MeOH (??) and this mixture was heated at reflux for 4 h. The resulting mixture was concentrated in vacuo and triturated with 1 N NaOH. The solid precipitate was filtered, washed with water and dried to give compound 3 as a solid: MS 329 ($MH^+$)

Example 4

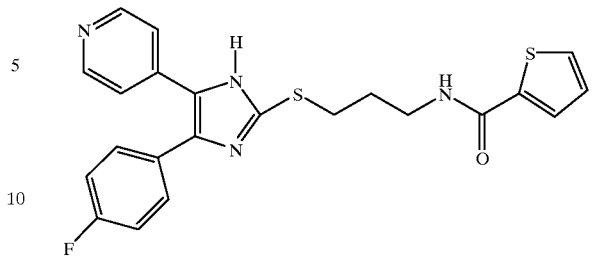

5(4)-(4-Fluorophenyl)-2-(3-(thien-2-ylamido)prop-1-yl)thio-4(5)-(4-pyridyl)-imidazole Cpd. 4

Sodium bicarbonate (0.42 g) and thiophenecarbonyl chloride (0.28 mL, 2.50 mmol) were added to a solution of compound 3 (0.75 g, 2.27 mmol) in DMF (6 mL) under $N_2$ at room temperature. This mixture was stirred for 45 min and poured into ice/$H_2O$. The resulting solid was filtered, washed with $H_2O$ and dried in vacuo to give compound 4 as a solid: mp 172–75° C.; MS 439 ($MH^+$).

Example 5

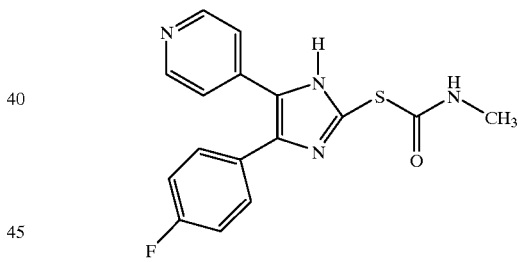

5(4)-(4-Fluorophenyl)-2-(N-methylaminocarbonyl)thio-4(5)-(4-pyridyl)-imidazole

Cpd. 5

95% Sodium Hydride (32 mg, 1.3 mmol) and methyl isocyanate (0.77 mL, 1.30 mmol) were added successively to a solution of 4-(4-fluorophenyl)-2-mercapto-5-(4-pyridyl)imidazole (350 mg, 1.30 mmol) and this mixture was stirred at room temperature for 2h. The resulting mixture was poured into $H_2O$ and the solid precipitate was filtered, washed with $H_2O$ and dried in vacuo to give compound 5 as a solid: mp>275° C.; MS 272 (M-$CONHCH_3$).

Example 6

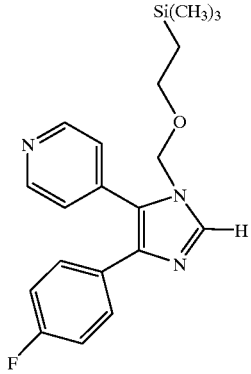

Cpd. 6a

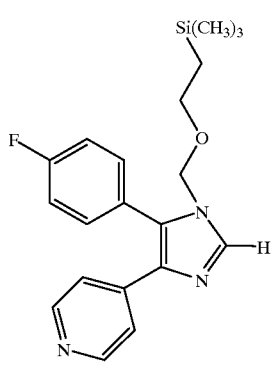

Cpd. 6b 4-(4-Fluorophenyl)-5-(4-pyridyl)-1-(2-(trimethylsilyl)ethoxymethyl)-imidazole Cpd. 6a 5-(4-Fluorophenyl)-4-(4-pyridyl)-1-(2-(trimethylsilyl)ethoxymethyl)-imidazole Cpd. 6b 60% Sodium Hydride (0.92 g, 23 mmol) was added to a stirred solution of 5(4)-(4-fluorophenyl)4(5)-(4-pyridyl)-imidazole (5.50 g, 23 mmol) in DMF under $N_2$. 2-(Trimethylsilyl)ethoxymethyl chloride (4.07 mL, 23 mmol) was added after 15 min and the resulting mixture was stirred for 3 h, poured into $H_2O$, dried ($MgSO_4$) and concentrated in vacuo. The resulting oil was purified by column chromatography on silica gel using ethyl acetate as an eluent. The less polar isomer crystallized to give compound 6a: mp 111–13° C.; MS 370 ($MH^+$). The more polar isomer crystallized to give compound 6b: mp 62–64° C.; MS 370 ($MH^+$).

Example 7

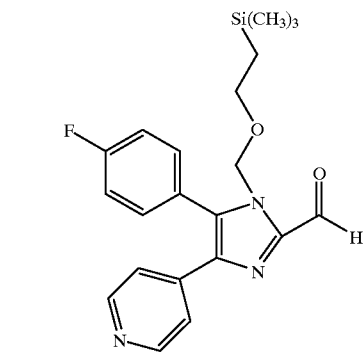

5-(4-Fluorophenyl)-4-(4-pyridyl)-1-(2-(trimethylsilyl)ethoxymethyl)-2-imidazole carboxaldehyde Cpd. 7 n-Butyl lithium (1.6 N, 13 mL, 21.0 mmol) was added to a stirred solution of compound 6b (7.10 g, 19.2 mmol) in THF at –77 to –78° C. This mixture was stirred for 15 min, DMF (2 mL, 26 mmol) was added and the resulting mixture was stirred at ambient temperature for about 1 h. The reaction was quenched with $H_2O$, extracted with ethyl acetate and concentrated in vacuo. The residue was purified by column chromatography on silica gel using ethyl acetate/hexane as an eluent to give compound 7 as a solid: mp 42–45° C.; MS 398 ($MH^+$).

Example 8

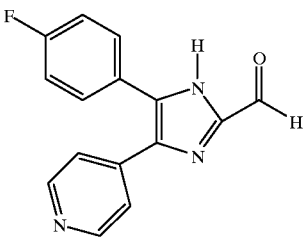

5(4)-(4-Fluorophenyl)-4(5)-(4-pyridyl)-2-imidazole carboxaldehyde

Cpd. 8

1N HCl (20 mL) was added to a solution of compound 7 (1.60 g) in EtOH (20 mLs). This mixture was stirred for 30 min, neutralized with $NaHCO_3$ and poured into $H_2O$. The solid precipitate was filtered and dried to give the title compound as a solid: mp 233–43° C. (dec.); MS 268 ($MH^+$).

Example 9

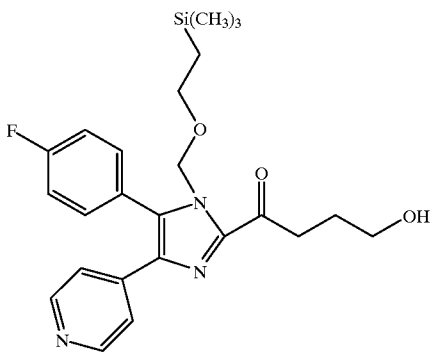

4-Hydroxy-1-[5-(4-fluorophenyl)-4-(4-pyridyl)-1-(2-(trimethylsilyl)ethoxymethyl)imidazol-2-yl]butanone Cpd. 9 n-Butyl lithium (1.6 N, 3.5 mL, 5.6 mmol) was added to a stirred solution of compound 6b (3.5 mL, 5.78 mmol) in THF at −77 to −78° C. This mixture was stirred for 15 min, α-butyrolactone (2 mL, 26 mmol) was added and the resulting mixture was stirred to ambient temperature. The reaction was quenched with $H_2O$, extracted with ethyl acetate and concentrated in vacuo. The residue was purified by column chromatography on silica gel using methylene chloride/MeOH 19:1, as an eluent to give compound 9 as a solid: mp 109.5–110.5° C.; MS 456 (MH$^+$).

Example 10

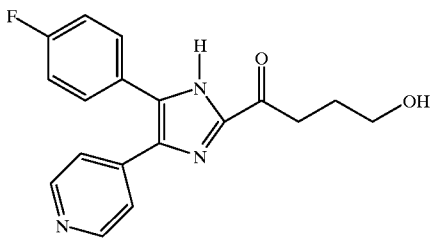

4-Hydroxy-1-[5-(4-fluorophenyl)-4-(4-pyridyl)-imidazol-2-yl]butanone

Cpd. 10

Cpd 9 (8.20 g, 1.8 mmol) was heated at reflux in 1 N HCl for 1 h. The mixture was cooled and neutralized with sodium bicarbonate. The resulting solid 20 precipitate was filtered and washed with $H_2O$ to give compound 10 as a solid: mp 205–07° C.

Example 11

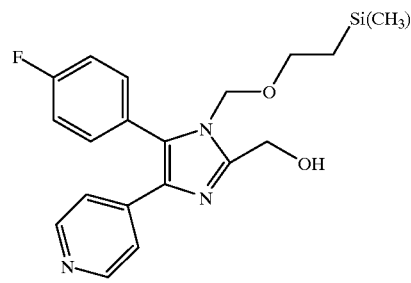

5-(4-Fluorophenyl)-2-hydroxymethyl-4-(4-pyridyl) 1-(2-(trimethylsilyl)ethoxymethyl) imidazole Cpd. 11

10% Palladium on carbon (3.0 g) was added to a solution of compound 7 (3.93 g, 9.89 mmol) in MeOH. This mixture was shaken under $H_2$ (40 psi) for 1h, filtered and concentrated in vacuo to give the title compound as a solid: mp 169–71° C., MS 400 (MH$^+$).

Example 12

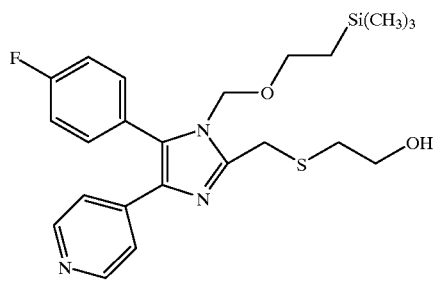

5-(4-Fluorophenyl)-2-[4-hydroxy-2-thiabut-1-yl]4-(4-pyridyl)-1-(2-(trimethylsilyl)ethoxymethyl) imidazole Cpd. 12

Triphenylphosphine (3.77 g, 14.4 mmol) and $CCl_4$ (1.39 mL, 14.4 mmol) were added to a solution of compound 11 (2.87 g, 7.18 mmol) in acetonitrile (70 mL) and the resulting mixture was stirred for 4 h. 2-Mercaptoethanol (2.52 mL, 35.9 mmol) and NaOH (2.44 g, 35.9 mmol) were added to the reaction and the resulting mixture was stirred for another 18 h and concentrated in vacuo. The residue was partitioned between water and ethyl acetate and the organic layer was concentrated in vacuo. This residue was purified by column chromatography on silica gel using ethyl acetate/hexane (1:1) to give the title compound as a solid: mp 74–76° C., MS 460 (MH$^+$).

Example 13

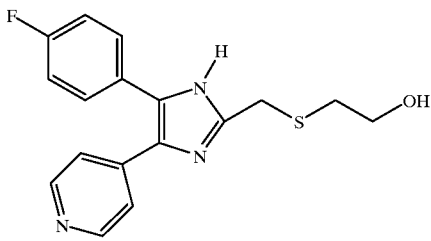

5-(4-Fluorophenyl)-2-[4-hydroxy-2-thiabut-1-yl]4-(4-pyridyl)-imidazole

Cpd. 13

A mixture of compound 12 (260 mg, 0.566 mmol) and 1N HCl (10 mL) was heated to 100° C. for 8 h. The resulting mixture was neutralized with sodium bicarbonate and the solid precipitate was filtered, washed with H$_2$O and dried to give the title compound as a solid: mp 227–29° C.; MS 330 (MH$^+$).

Example 14

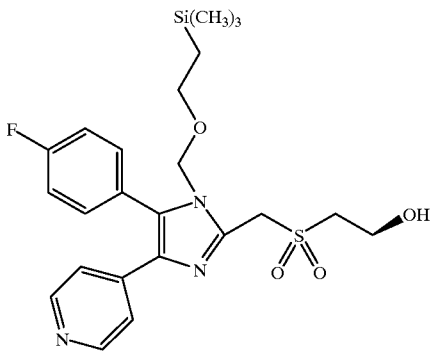

5-(4-Fluorophenyl)-2-[4-hydroxy-2-sulfonyl-but-1-yl]4-(4-pyridyl)-1-(2-(trimethylsilyl)ethoxymethyl) imidazole Cpd. 14

A solution of oxone (2.00 g, 3.25 mmol) in H$_2$O (100 mL) was added to a stirred solution of compound 12 (0.50 g, 1.09 mmol) in MeOH (100 mL). This mixture was stirred for 4 h at ambient temperature concentrated in vacuo and extracted with methylene chloride. The combined organic layer was dried and concentrated to a residue. This residue was purified by column chromatography using methylene chloride:MeOH (19:1) as an eluent to give the title compound as a solid: mp 45–48° C.; MS 492(MH$^+$).

Example 15

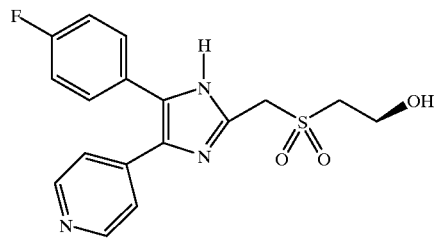

5-(4-Fluorophenyl)-2-[4-hydroxy-2-sulfonyl-but-1-yl]-4-(4-pyridyl)-imidazole

Cpd. 15

A solution of compound 14 (343 mg, 0.698 mmol) and 1N HCl was stirred at 90° C. for 2 h. This mixture was neutralized with sodium bicarbonate and the resulting solid precipitate was washed with water to give the title compound: mp 232–237° C.; MS 362 (MH$^+$).

Example 16

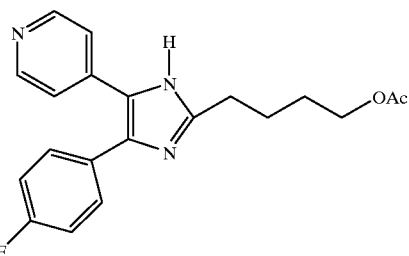

16a

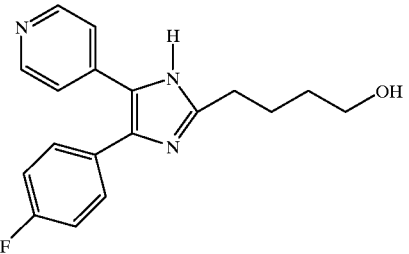

16b

4-[5(4)-(4-Fluorophenyl)-(5)-(4-pyridyl)imidazol-2-yl]butayl acetate

Cpd. 16a

4-[5(4)-(4-Fluorophenyl)4(5)-(4-pyridyl)imidazol-2-yl]butanol

Cpd. 16b

5-Hydroxy pentanal (0.97 mL) and ammonium acetate (5.60 g, 72.7 mmol) were added to a solution of 1-(4-fluorophenyl)-2-(4-pyridyl)-1,2-ethandione (2.08 g, 9.08 mmol) in acetic acid (50 mL) and the mixture was heated at reflux for 1 h. The resulting mixture was cooled to about 0° C. and the ammonium hydroxide was added until the mixture reached a pH of 8. This mixture was extracted with ethyl acetate and purified on silica gel using methylene chloride:

methanol (9:1) as an eluent, where compound 12a was isolated as the least polar product: MS 354 (MH+) and compound 12b was isolated as the most polar product: mp 213–214.5° C., MS 312 (MH+).

Example 17

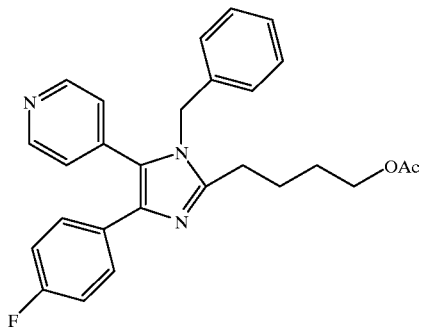

Cpd. 17

4-[1-Benzyl-4-(4-fluorophenyl)-5-(4-pyridyl) imidazol-2-yl]butyl acetate

Cpd. 17

Sodium hydride (0.112 g, 2.88 mmol) was added to a solution of compound 16a (1.00 g, 2.80 mmol) in DMF (50 mL) and the mixture was stirred for 30 min. Benzyl bromide (0.34 mL, 2.80 mmol) was added and this mixture was stirred for 2.5 h at ambient temp and poured into water. The aqueous mixture was extracted with ethyl acetate and the combined organic extracts were concentrated in vacuo and purified by column chromatography using ethyl acetate as an eluent to give compound 17 as an oil: MS 444 (MH+).

Example 18

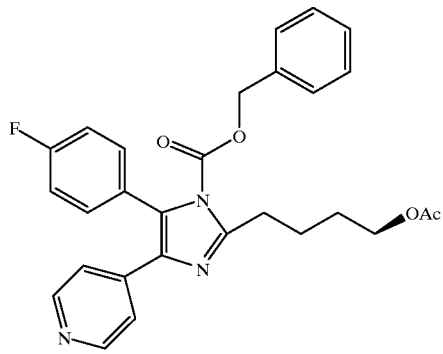

4-[1-Benzyloxycarbonyl-4-(4-fluorophenyl)-5-(4-pyridyl)imidazol-2-yl]-butyl acetate Cpd. 18

Triethylamine (0.4 mL) and benzyl chloroformate (0.20 mL, 1.40 mmol) was added to a solution of compound 16a. This mixture was stirred for 2 h at ambient temperature, concentrated in vacuo and partitioned between methylene chloride and H₂O. The organic extracts were concentrated in vacuo to give compound 18 as a solid: mp 97–101° C.; MS 488 (MH+).

Example 19

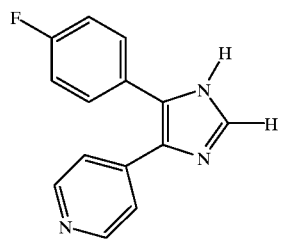

5(4)-(4-Fluorophenyl)- 4(5)-(4-pyridyl)imidazole

Cpd. 19

A solution of selenium dioxide (4.82 g, 43.4 mmol) in H₂O (20 mL) was added to a solution of 1-(4-fluorophenyl)-2-(4-pyridyl)-2-ethanone (9.33 g, 43.4 mmol) in dioxane (100 mL) and the resulting mixture was heated at reflux for 2 h. This mixture was concentrated in vacuo, triturated with ethyl acetate and filtered. The residue was purified by column chromatography using ethyl acetate/hexane (1:1) as an eluent to give 1-(4-fluorophenyl)-2-(4-pyridyl)-1,2-ethandione. A mixture of ammonium acetate (25.25 g, 0.328 mol) and hexamethylenetetraamine (9.18 g, 65.5 mmol) was added to a solution of the isolated dione dissolved in acetic acid (150 mL). This mixture was stirred at 80° C. for 2 h, poured into concentrated ammonium hydroxide (200 mL) and the resulting precipitate was filtered, washed with H₂O and dried to give the title compound as a solid: mp 242–44.3° C.; MS 240 (MH+).

BIOLOGICAL EXAMPLES

One of the biological activities of the compounds of the invention was demonstrated by in vitro and in vivo assays. As discussed previously, agents which inhibit the activity of the enzyme p38, inhibit the production of the inflammatory cytokines TNF-α and IL-1. Compounds of the invention were measured for their ability to inhibit the activity of p38 by the following in vitro assay.

Example 20

A solution (38 µL) of purified recombinant p38 (where the amount of enzyme was determined empirically considering the linear range of the assay and the acceptable signal to noise ratio; 6xHis-p38 expressed in *E.coli*), myelin basic protein substrate (also determined empirically), a buffer of pH 7.5 (Hepes:25 mM, MgCl₂:10 mM, MnCl₂:10 mM) were added to 92 wells of a 96-well round bottom polypropylene plate. The remaining wells were used for control ("CTRL") and background ("BKG"). The CTRL was prepared with the enzyme, substrate buffer and 2% DMSO, and the BKG was prepared with substrate buffer and 2% DMSO. A solution (12 µL) of the test compound in DMSO (compounds were diluted to 125 µM in 10% DMSO/H₂O and assayed at 25 µM where the final DMSO concentration was 2%) was added to the testing wells. The ATP/³³P-ATP solution (10 µL: containing 50 µM unlabeled ATP and 1 µCi ³³P-ATP) was added to all wells and the completed plates were mixed and incubated at 30° C. for 30 min. Icecold 50% TCA/10 mM sodium phosphate (60 µL) were added to each well and the plates were kept on ice for 15 min. The contents of each well were transferred to the wells of a 96-well filterplate (Millipore, MultiScreen-DP) and the filterplate was placed on a vacuum manifold, fitted with a waste collection tray. The wells were washed five times with 10% TCA/10 mM sodium phosphate (200 μL) under vacuum. MicroScint-20 scintillant was added, the plates were sealed using Topseal-S sheets and counted in a Packard TopCount scintillation counter using a $^{33}$P liquid program with color quench correction, where the output is in color quench-corrected cpm. The % inhibition of the test compounds was calculated by the following formula: % inhibition=[1-(sample -BKG)/(CTRL-BKG)]×100. This data is shown in Table A.

Although compounds were initially tested at 25 μM, if warranted the compounds were tested at 4-fold increments above and below that concentration. In addition, IC$_{50}$s were calculated for some compounds using the Deltagraph 4-parameter curve fitting program.

Example 21

In addition to the enzyme assay, the compounds of the invention were tested in an in vitro whole cell assay using peripheral blood mononuclear cells ("PBMC") which were obtained from human blood as follows. Freshly obtained venous blood was anticoagulated with heparin, diluted with an equal volume of phosphate buffered saline ("PBS") and placed in a sterile tube or other container. Aliquots (30 mL) of this mixture were transferred to centrifuge tubes which were underlaid with Ficoll-Hypaque (15 mL). The prepared tubes were centrifuged at 400×g without braking for 30 min at room temperature. Approximately ½ to ⅔ of the platelet layer above the mononuclear cell band was removed with a pipet. The majority of the mononuclear cell layer was carefully removed using a pipet and these PBMCs were diluted with PBS and spun at 600×g for 15 min. The resulting PBMCs were washed with another portion of PBS and spun at 400×g for 10 min at room temperature. The recovered pellets were diluted in low endotoxin RPMI/1% FCS culture medium and gave a cell concentration of 0.5–2.0 X 10$^6$ PMBC/mL. A small volume of the suspension was removed for counting on a hemocytometer and the remaining preparation was centrifuged at 200×g for 15 min at room temperature. The recovered pelleted PMBC were resuspended in RPMI/1% FCS to a concentration of 1.67× 10$^6$/mL.

To run the assay, the PBMC suspension (180 μL) was transferred to duplicate wells of a 96-well flat-bottom microtiter plate and incubated for 1 h at 37° C. A solution of test compound (10 μL: prepared at 20×the desired final concentration) was added to each well and the plate was incubated for 1 h at 37° C. A solution (10 μL) of LPS in RPMI/1% FCS (200 ng/mL) was added and the wells were incubated overnight at 37° C. The supernate (100 μL) was removed from each well and diluted with RPMI/1% FCS (400 μL). The samples were analyzed for TNF-α using a commercial ELISA kit (Genzyme). This data is shown in Table A. In addition to the biological data, the synthetic schemes which may be used to prepare the compounds are listed. Since imidazoles which are unsubstituted at the 1-position are subject to tautomerization, the substituents listed for $R_1$ and $R_2$ are interchangeable when $R_3$ is hydrogen.

TABLE A

| Cpd. # | $R_1$ | $R_2$ | $R_3$ | $R_4$ | CPSB IC$_{50}$ μm | TNF-α IC$_{50}$ nm | Scheme |
|---|---|---|---|---|---|---|---|
| 1 | 4-F—Ph | 4-pyr | H | S—(CH$_2$)$_2$CH$_3$ | 0.68 | | 1 |
| 2 | 4-F—Ph | 4-pyr | H | S—(CH$_2$)$_3$PHT | 0.79–1.8 | 1000 | 1 |
| 3 | 4-F—Ph | 4-pyr | H | S—(CH$_2$)$_3$NH$_2$ | 26% @ 20 μm | | 1 |
| 4 | 4-F—Ph | 4-pyr | H | S—(CH$_2$)$_3$NHC(O)-2-thienyl | 1.25 | 10 | 2 |
| 5 | 4-F—Ph | 4-pyr | H | SC(O)NHCH$_3$ | 81% @ 20 μm | | 1 |
| 8 | 4-F—Ph | 4-pyr | H | C(O)H | 0.8 | 140 | 3 |
| 9 | 4-pyr | 4-F—Ph | SEM | C(O)(CH$_2$)$_3$OH | | >10000 | 3 |
| 10 | 4-F—Ph | 4-pyr | H | C(O)(CH$_2$)$_3$OH | | 400 | 3 |
| 13 | 4-F—Ph | 4-pyr | H | CH$_2$S(CH$_2$)$_2$OH | | 80 | 4 |
| 15 | 4-F—Ph | 4-pyr | H | CH$_2$SO$_2$(CH$_2$)$_2$OH | | 40 | 5 |
| 16a | 4-pyr | 4-F—Ph | H | (CH$_2$)$_4$OAc | 1.42 | | 6 |
| 16b | 4-F—Ph | 4-pyr | H | (CH$_2$)$_4$OH | 1.59 | 10 | 6 |
| 17 | 4-F—Ph | 4-pyr | CH$_2$PH | (CH$_2$)$_4$OAc | 2.63 | 500 | 6 |
| 18 | 4-pyr | 4-F—Ph | CO$_2$CH$_2$Ph | (CH$_2$)$_4$OAc | 10% @ 5 μm | | 6 |
| 20 | 4-F—Ph | 4-pyr | H | S(CH$_2$)$_2$CH(OCH$_2$CH$_3$)$_2$ | 2.0 | | 1 |
| 21 | 4-F—Ph | 4-pyr | H | SH | 1.9 | | 1 |
| 22 | 4-F—Ph | 4-pyr | H | SCH(CH$_3$)$_2$ | 0.47 | | 1 |
| 23 | 4-F—Ph | 4-pyr | H | SCH$_2$-cyclopropyl | 1.0–1.8 | | 1 |
| 25 | 4-F—Ph | 4-pyr | H | S(CH$_2$)$_2$PHT | 52% @ 5 μm | 500 | 1 |
| 26 | 4-F—Ph | 4-pyr | H | S(CH$_2$)$_3$NHC(O)Ph | 2.18 | 100 | 2 |
| 27 | 4-F—Ph | 4-pyr | H | S(CH$_2$)$_4$PHT | 2.46 | 2000 | 1 |
| 28 | 4-F—Ph | 4-pyr | H | S—(CH$_2$)$_3$NH—C(O)-1 naphthyl | 1.25 | 97 | 2 |
| 29 | 4-F—Ph | 4-pyr | H | S—(CH$_2$)$_3$NH—C(O)-2-furanyl | 91% @ 20 μm | 112 | 2 |
| 30 | 4-F—Ph | 4-pyr | H | S—(CH$_2$)$_3$NH—S(O)$_2$—Ph | 92% @ 20 μm | 100 | 2 |

TABLE A-continued

| Cpd. # | $R_1$ | $R_2$ | $R_3$ | $R_4$ | CPSB $IC_{50}$ μm | TNF-α $IC_{50}$ nm | Scheme |
|---|---|---|---|---|---|---|---|
| 31 | 4-F—Ph | 4-pyr | H | S—(CH$_2$)$_3$NH—C(O)-2-naphthyl | | 275 | 2 |
| 32 | 4-F—Ph | 4-pyr | H | S(CH$_2$)$_3$—NHS(O)$_2$CH$_3$ | | 150 | 2 |
| 33 | 4-F—Ph | 4-pyr | H | CH$_2$S(CH$_2$)$_2$PHT | | 200 | 4 |
| 34 | 4-F—Ph | 4-pyr | H | S(CH$_2$)$_3$NHC(O)CH$_3$ | | 200 | |
| 35 | 4-F—Ph | 4-pyr | H | CH$_2$S(CH$_2$)$_2$CH$_3$ | | 30 | 4 |
| 36 | 4-pyr | 4-F—Ph | SEM | CH$_2$OH | 6% @ 5 μm | | |
| 37 | 4-F—Ph | 4-pyr | H | SCH$_2$CHCH$_2$ | 0.75 | | 1 |
| 38 | 4-F—Ph | 4-pyr | H | SCH$_2$CN | 0.4 | | 1 |
| 39 | 4-F—Ph | 4-pyr | H | SCH$_2$CH$_3$ | 0.4 | | 1 |
| 40 | 4-F—Ph | 4-pyr | H | S(CH$_2$)$_3$CH$_3$ | 0.28–0.7 | | 1 |
| 41 | 4-F—Ph | 4-pyr | H | S(CH$_2$)$_9$CH$_3$ | >10,000 | | 1 |
| 42 | 4-pyr | 4-F—Ph | CH$_2$Ph | (CH$_2$)$_4$OAc | 2% @ 5 μm | | 6 |
| 43 | 4-pyr | 4-F—Ph | CH$_2$Ph | (CH$_2$)$_4$PHT | 8% @ 5 μm | | 6 |
| 44 | 4-F—Ph | 4-pyr | SEM | (CH$_2$)$_4$OAc | 74% @ 20 | 150 | 6 |
| 45 | 4-pyr | 4-F—Ph | SEM | (CH$_2$)$_4$OAc | 8% @ 20 μm | –inactive | 6 |
| 46 | 4-pyr | 4-F—Ph | SEM | (CH$_2$)$_4$OH | 9% @ 20 μm | inactive | 6 |
| 47 | 4-pyr | 4-F—Ph | H | (CH$_2$)$_4$PHT | | 283 | 6 |
| 48 | 4-F—Ph | 4-pyr | CH$_2$Ph | (CH$_2$)$_4$PHT | | 1750 | 6 |
| 49 | 4-F—Ph | 4-pyr | H | CH$_2$OH | | 250 | 4 |
| 50 | 4-pyr | 4-F—Ph | (CH$_2$)$_3$PHT | (CH$_2$)$_4$OAc | | 150 | 6 |
| 51 | 4-F—Ph | 4-pyr | (CH$_2$)$_3$PHT | (CH$_2$)$_4$OH | | 175 | 6 |
| 52 | 4-pyr | 4-F—Ph | (CH$_2$)$_3$PHT | (CH$_2$)$_4$OH | | 200 | 6 |
| 53 | 4-F—Ph | 4-pyr | (CH$_2$)$_3$PHT | CH$_2$O(CH$_2$)$_3$PHT | | 175 | 4 |
| 54 | 4-pyr | 4-F—Ph | (CH$_2$)$_3$PHT | CH$_2$O(CH$_2$)$_3$PHT | | 200 | 4 |
| 55 | 4-pyr | 4-F—Ph | (CH$_2$)$_3$PHT | CH$_2$OH | | 1250 | 4 |
| 56 | 4-F—Ph | 4-pyr | (CH$_2$)$_3$PHT | CH$_2$OH | | 30 | 4 |
| 57 | 4-pyr | 4-F—Ph | SEM | CH$_2$SO$_2$C$_3$H$_7$ | | 5000 | 5 |
| 58 | 4-F—Ph | 4-pyr | (CH$_2$)$_3$PHT | CH$_2$O CH$_3$ | | 75 | 6 |
| 59 | 4-pyr | 4-F—Ph | H | CH$_2$SO$_2$C$_3$H$_7$ | | 55 | 5 |
| 60 | 4-pyr | 4-F—Ph | (CH$_2$)$_3$PHT | CH$_2$OCH$_3$ | | 400 | 6 |
| 61 | 4-F—Ph | 4-pyr | (CH$_2$)$_3$PHT | (CH$_2$)$_2$OC$_2$H$_5$ | | 200 | 6 |
| 62 | 4-F—Ph | 4-pyr | (CH$_2$)$_3$PHT | CH$_3$ | | 362 | 6 |
| 63 | 4-pyr | 4-F—Ph | (CH$_2$)$_3$PHT | CH$_3$ | | 17 | 6 |
| 64 | 4-F—Ph | 4-pyr | (CH$_2$)$_3$PHT | C$_2$H$_5$ | | 80.0 | 6 |
| 65 | 4-pyr | 4-F—Ph | (CH$_2$)$_3$PHT | C$_2$H$_5$ | | 20.0 | 6 |
| 66 | 4-F—Ph | 4-pyr | (CH$_2$)$_3$Ph | C$_2$H$_5$ | | 6 | 6 |
| 67 | 4-pyr | 4-F—Ph | (CH$_2$)$_3$Ph | C$_2$H$_5$ | | 300 | 6 |
| 68 | 4-F—Ph | 4-pyr | (CH$_2$)$_3$Ph | CH$_3$ | | 1.5 | 6 |
| 69 | 4-pyr | 4-F—Ph | (CH$_2$)$_3$Ph | CH$_3$ | | 100 | 6 |
| 70 | 4-pyr | 4-F—Ph | (CH$_2$)$_3$PHT | H | | 500 | 7 |
| 71 | 4-F—Ph | 4-pyr | (CH$_2$)$_3$PHT | H | | 39 | 7 |
| 72 | 4-pyr | 4-F—Ph | (CH$_2$)$_4$PHT | H | | 300 | 7 |
| 73 | 4-F—Ph | 4-pyr | (CH$_2$)$_4$PHT | H | | 500 | 7 |
| 74 | 4-F—Ph | 4-pyr | (CH$_2$)$_3$Ph | Br | | 200 | 7 |
| 75 | 4-F—Ph | 4-pyr | (CH$_2$)$_3$Ph | I | | 3 | 7 |
| 76 | 4-pyr | 4-F—Ph | (CH$_2$)$_4$PHT | I | | 800 | 7 |
| 77 | 4-F—Ph | 4-pyr | (CH$_2$)$_4$PHT | I | | 445 | 7 |
| 78 | 4-F—Ph | 4-(2-butyl)pyr | (CH$_2$)$_3$Ph | CH$_2$OH | | 450 | 4 |
| 79 | 4-pyr | 4-F—Ph | CH$_2$COC$_2$H$_5$ | H | | 600 | |
| 80 | 4-F—Ph | 4-pyr | CH$_2$COC$_2$H$_5$ | H | | 200 | |
| 81 | 4-pyr | 4-F—Ph | (CH$_2$)$_3$-3-pyr | H | | 500 | |
| 82 | 4-F—Ph | 4-pyr | (CH$_2$)$_3$-3-pyr | H | | 20 | |
| 83 | 4-pyr | 4-F—Ph | (CH$_2$)$_3$-4-pyr | H | | 1000 | |
| 84 | 4-F—Ph | 4-pyr | (CH$_2$)$_3$-4-pyr | H | | 10 | |
| 85 | 4-pyr | 4-F—Ph | (CH$_2$)$_2$-OPh | H | | 2000 | |
| 86 | 4-F—Ph | 4-pyr | (CH$_2$)$_2$-OPh | H | | 40 | |

Example 22

The IL-1 B modulating activity of compounds of the invention was determined by the following in vitro assay. Plastic-adherent cells were prepared from PBMC. Briefly, PBMCs were added the wells of a 96-well plate as above, incubated for 1 h at 37° C., and the adherent cells prepared by gently resuspending the non-adherent cells with a pipetor, removing and discarding them and gently washing the wells 3 times with 200 μL culture medium. Additional culture medium (180 μL) was added to the wells after the final wash. Compound addition, LPS stimulation, incubation and supernate harvest were as for TNF-α. Supernatant were assayed for interleukin-1β using a commercial ELISA (Genzyme).

Compounds 10, 28 and 59 inhibited the production of IL-1B at $IC_{50}$s of 800, 86 and 350 nM, respectively.

Example 23

The ability of the compounds of Formula I to inhibit LPS induced TNF-α production was demonstrated in the following in vivo rodent assays. Mice (BALB/cJ females, Jackson Laboratories) or rats (Lewis males, Charles River) were fasted for 30 min prior to oral dosing with 5–10 mL/kg of test compound at 5–50 mg/kg. Thirty minutes after dosing, the animals were injected intraperitoneally with LPS at 1 mg/kg and returned to their cages for I h. Animals were anesthetized by $CO_2$, exsanguinated by cardiac puncture and whole blood collected (0.1–0.7 mL). The blood was allowed to clot and serum was transferred to a centrifuge tube. This sample was centrifuged, serum was collected, aliquoted and frozen at –80° C. Samples were tested by commercial ELISAs for TNF-α (Endogen for mouse TNF-α and Biosource for rat TNF-α). Compounds 15 and 56 inhibited TNF-α production in the mouse at 88% and 37% respectively at a dose of 25 mg/kg.

What is claimed is:

1. A compound of Formula I

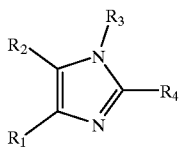

wherein:
one of R1 and R2 is phenyl optionally substituted by one or more of the members of the group consisting of C1–5 alkyl, halogen, nitro, trifluoromethyl and nitrile; the other is pyridyl optionally substituted by one or more of the members of the group consiting of C1–5alkyl and halogen;

$R_3$ is hydrogen, SEM, $C_{1-5}$alkoxycarbonyl, aryloxycarbonyl, aryiC$_{1-5}$alkyloxycarbonyl, arylC$_{1-5}$alkyl, phthalimidoC$_{1-5}$alkyl, aminoC$_{1-5}$alkyl, diaminoC$_{1-5}$alkyl, succinmidoC$_{1-5}$alkyl, C$_{1-5}$alkylcarbonyl, arylcarbonyl, C$_{1-5}$alylcarbonylC$_{1-5}$alkyl, aryloxycarbonylC$_{1-5}$alkyl, or substituted arylC$_{1-5}$alkyl wherein the aryl substituents are independently selected from one or more members of the group consisting of $C_{1-5}$alkyl, $C_{1-5}$alkoxy, halogen, amino, $C_{1-5}$alkylamino, and di$C_{1-5}$alkylamino;

$R_4$ is $(A)_n$-$(CH_2)_q$-X wherein:
A is sulfur;
n is 1;
q is 0–9;
X is selected from the group consisting of amino, $C_{1-5}$alkylamino, phthalimido, amido, phenylcarbonyl, $C_{1-5}$alkylaminocarbonyl, phenylaminocarbonyl, arylC$_{1-5}$alkylaminocarbonyl, $C_{1-5}$alkylsulfonyl, phenylsulfonyl,
substituted amido
wherein the carbonyl substituent is selected from the group consisting of $C_{1-5}$alkyl, phenyl, arylC$_{1-5}$alkyl, thienyl, furanyl, and naphthyl,
substituted phenylcarbonyl
wherein the phenyl substituents are independently selected from one or members of the group consisting of $C_{1-5}$alkyl, halogen and $C_{1-5}$alkoxy,
substituted $C_{1-5}$alkylsulfonyl
wherein the alkyl substituent is selected from the group consisting of hydroxy and phthalimido,
substituted phenylsulfonyl
wherein the phenyl substituents are independently selected from one or members of the group consisting of bromine, fluorine, chlorine, $C_{1-5}$alkoxy and trifluoromethyl, with the proviso:
if A is sulfur and X is other than, $C_{1-5}$alkylaminocarbonyl, phenylarninocarbonyl, arylC$_{1-5}$alkylaminocarbonyl, $C_{1-5}$alkylsulfonyl or phenylsulfonyl, then q must be equal to or greater than 1;

and pharmaceutically acceptable salts thereof.

2. The compound of claim 1 where $R_1$ is substituted phenyl and $R_2$ is pyridin-2-yl, pyridin-3-yl, pyridin4-yl.

3. The compound of claim 2 where $R_1$ is 4-fluorophenyl and $R_2$ is pyridin-4-yl.

4. The compound of claim 3 where $R_3$ is hydrogen, $C_{1-5}$alkyl, arylC$_{1-5}$alkyl, or substituted arylC$_{1-5}$alkyl.

5. The compound of claim 4 where $R_3$ is hydrogen or phenylC$_{1-5}$alkyl.

6. The compound of claim 5 where q is 0–6.

7. The compound of claim 6 where X is phthalimido, amido, substituted amido, $C_{1-5}$alkylsulfonyl, hydroxyC$_{1-5}$alkylsulfonyl, phenylsulfonyl, substituted phenylsulfonyl, or substituted amido.

8. A compound and pharmaceutically acceptable salts thereof selected from 5(4)-(4-fluorophenyl)-2-(3-(naphth-1-ylamido)prop-1-yl)thio-4(5)-(4-pyridyl)-imidazole (Cp#28); 5(4)-(4-fluorophenyl)-2-(3-(phenylsulfonamido) prop-1-yl)thio-4(5)-(4-pyridyl)-imidazole (Cp#30).

9. A pharmaceutical composition comprising a compound according to claim 1 and a pharmaceutically acceptable carrier or diluent.

10. A pharmaceutical composition comprising a compound according to claim 7 and a pharmaceutically acceptable carrier or diluent.

* * * * *